United States Patent [19]
Brandt et al.

[11] Patent Number: 5,508,201
[45] Date of Patent: Apr. 16, 1996

[54] METHOD FOR DIAGNOSING THE PRESENCE OR ABSENCE OF ONCOLOGICAL DISEASE

[75] Inventors: Nicolai B. Brandt; Yuri M. Petrousevich; Galina P. Petrova; Elana A. Pappysh, all of Moscow, Russian Federation; Hafez T. Farouqe, Amman, Jordan; Kaspar A. Kasparian, Raleigh, N.C.

[73] Assignee: Hanader Medical Corporation, Wake Forest, N.C.

[21] Appl. No.: 38,347

[22] Filed: Mar. 19, 1993

[51] Int. Cl.$^6$ ............................................. G01N 33/49
[52] U.S. Cl. ............................ 436/64; 436/63; 436/164; 436/909; 73/61.48
[58] Field of Search ........................... 436/64, 909, 63, 436/149, 164, 811, 813; 422/82.05; 356/339; 73/61.48

[56] References Cited

U.S. PATENT DOCUMENTS

| | | | |
|---|---|---|---|
| 4,063,892 | 12/1977 | Vassilev et al. | 436/64 |
| 4,696,905 | 9/1987 | Aoyama et al. | 436/64 |
| 4,767,717 | 8/1988 | Baisden | 436/64 |
| 4,912,050 | 3/1990 | Fossel | 436/64 |
| 4,918,021 | 4/1990 | Fossel | 436/64 |

*Primary Examiner*—James C. Housel
*Assistant Examiner*—Rachel Heather Freed
*Attorney, Agent, or Firm*—John G. Mills and Associates

[57] ABSTRACT

The invention pertains to a method for diagnosing oncological diseases wherein an effective small amount of blood is obtained, such as from a finger, and a solution containing blood plasma or serum is exposed to laser radiation and the values of one or more parameters are determined upon measurements at molecular level. Said parameters are then compared with analogous measured or established parameters of a reference solution to determine whether there are significant variations or similarities which indicate the absence or presence of oncological diseases or a predisposition to same. In a preferred embodiment of the invention, blood plasma or serum is diluted in water up to 25% of the volume and the solution is then exposed to laser radiation in the standard mode. Measurements and determinations are then made of the coefficient of Rayleigh light scattering "R" in the solution and other indicative parameters such as the effective mass "M" and a parameter of molecular interaction "B" of scattered particles in the solution. The values of R, M and B are then compared with respective reference indicative parameters $R_{ref}$, $M_{ref}$ and $B_{ref}$ of a calculated or established reference standard or a reference solution, such as one obtained from the blood serum of healthy individuals. If $R/R_{ref} > 2$, $M > M_{ref}$ and $B < B_{ref}$, then an oncological disease is diagnosed.

37 Claims, 7 Drawing Sheets

| HEALTHY PERSONS WITHOUT ONCOLOGICAL DISEASES | | | | | PATIENTS WITH ONCOLOGICAL DISEASES | | | |
|---|---|---|---|---|---|---|---|---|
| Test No. | R/Rref | M($10^4$) | B($10^{-6}$) | Health Status | R/Rref | M($10^4$) | B($10^{-6}$) | Cancer |
| 1 | 1.0 | 10.1 | 300 | Healthy | 2.2 | 56.3 | 0.015 | Stomach Cancer |
| 2 | 1.0 | 9.2 | 2400 | Healthy | 4.0 | | -.04 | Stomach Cancer |
| 3 | 1.3 | 10.8 | 2600 | Healthy | 3.2 | | -1.15 | Throat Cancer |
| 4 | 1.1 | 18.5 | 400 | Healthy | 2.0 | 41.2 | 0.25 | Cervical Cancer |
| 5 | 1.0 | 9.8 | 550 | Healthy | 2.5 | | -0.15 | Uterine Cancer |
| 6 | 1.5 | 9.2 | 200 | Ulcer | 3.6 | | -0.85 | Cervical Cancer |
| 7 | 1.0 | 13.3 | 400 | Healthy | 3.9 | | -10 | Throat Cancer |
| 8 | 1.1 | 12.5 | 250 | Gastritis | 3.3 | 61.0 | 0.015 | Cervical Cancer |
| 9 | 1.0 | 11.8 | 1500 | Healthy | 3.5 | | -209 | Stomach Cancer |
| 10 | 1.1 | 10.8 | 1200 | Healthy | 2.5 | 38.6 | 0.005 | Uterine Cancer |
| 11 | | | | | 3.5 | | -0.9 | Stomach Cancer |
| 12 | | | | | 3.3 | | -1.5 | Breast Cancer |

FIGURE 2

| Test No. | R/Rref Healthy | R/Rref w. Cancer |
|---|---|---|
| 1 | 1.0 | 2.2 |
| 2 | 1.0 | 4.0 |
| 3 | 1.3 | 3.2 |
| 4 | 1.1 | 2.0 |
| 5 | 1.0 | 2.5 |
| 6 | 1.5 | 3.6 |
| 7 | 1.0 | 3.9 |
| 8 | 1.1 | 3.3 |
| 9 | 1.0 | 3.5 |
| 10 | 1.1 | 2.5 |

| Test No. | M($10^4$) Healthy | M($10^4$) w. Cancer |
|---|---|---|
| 1 | 10.1 | 56.3 |
| 4 | 18.5 | 41.2 |
| 8 | 12.5 | 61.0 |
| 10 | 10.8 | 38.6 |

| Test Number | 1 | 2 | 3 | 4 | 5 | 6 | 7 | 8 | 9 | 10 |
|---|---|---|---|---|---|---|---|---|---|---|
| $B(10^{-6})$ Healthy | 300 | 2400 | 2600 | 400 | 550 | 200 | 400 | 250 | 1500 | 1200 |
| $B(10^{-6})$ w. Cancer | 0.015 | -0.04 | -1.15 | 0.25 | -0.15 | -0.85 | -10 | 0.015 | -209 | 0.05 |

- Photon Correlator With 16 Bit Or More Computer/Processor

- Color Monitor, EGA, VGA, SVGA Or Better

- Round, Square And Buchard Specimen Cells

- Printer - Dot Matrix or Laser

- Laser Source, Such As Uniphase Argon-Ion Laser 75mw (448nm)

- Wide Bore Capillary Tubes

- Electrophoresis Measurement Kit

FIGURE 7

METHOD FOR DIAGNOSING THE PRESENCE OR ABSENCE OF ONCOLOGICAL DISEASE

FIELD OF THE INVENTION

This invention relates to medicine and in particular to the early diagnosis of oncological diseases through measurements of optical and other parameters of blood plasma or serum at molecular level.

BACKGROUND OF THE INVENTION

The fear of developing oncological diseases, the number of people dying of same and the devastations caused by these diseases are indeed factors that create a morbid fear of cancer for many. Ironically, those who are diagnosed as having the disease are too often told that their survival from the disease would have been enhanced if diagnosis had been made early. Yet a simple, inexpensive, untraumatic, reliable and quick method for diagnosis of the presence or absence of oncological disease in an individual has not been available. Nor have there been means for affecting mass screening of the population in a practical and affordable way or for assessing risk factors along with recommending more periodic check-ups based on calculated and observed parameters.

Diagnostic methods so far have mainly been applied to certain parts of the body, such as the colon, the breasts, the prostate and the uterus. Ironically again, such methods can and do miss other areas of the body that may meanwhile be affected by oncological diseases and have not been reliable and have not assessed risk factors and resulted in a recommendation for more frequent monitoring. Often the examinations and other approaches, such as exploratory surgery and biopsies, help diagnose oncological disease that has already progressed to become visible and palpable.

A simple, quick, reliable, affordable method of diagnosing the presence or absence of oncological diseases can obviously save millions of lives through allowing routine testing and mass screening as well as assessing risk factors and developing criteria for recommending more frequent monitoring for certain individuals. The method of the invention meets all these requirements.

It is known that cancer starts and progresses and that the sooner it is diagnosed, the better is the chance of survival. The method of this invention performs an analysis at the molecular level, or where there are early indications of the development of oncological diseases. The method of the invention is the product of extensive research conducted on a molecular level on the "common denominator" and indicative fluids of the human body such as both blood plasma and serum. Comprehensive measurements at molecular level and determinations of parameters related to these fluids, especially blood serum, have revealed significant differences in the values of certain parameters in patients with oncological diseases and for healthy individuals, leading to this invention.

DESCRIPTION OF THE PRIOR ART

The present invention has not been found in prior art, nor does prior art suggest or teach anything resembling the method of this invention. The search did not uncover issued patents and publications relevant to this invention. Also a computer search was conducted for medical, chemical and foreign patent application data bases which might have been used as references against a patent application for this invention. In the course of a search, Medline was searched from 1966. Further a search was conducted in the World Patent Index. In addition, the Magazine Index for patents and publications and patents was searched with respect to the detection and diagnosis of cancer.

The most relevant prior art uncovered in the course of the search is the following:

Canadian Patent No. 1 200 477; issued Feb. 11, 1986 to Lyke and Ware for Method For Detecting Luminescence in Living Cell System National Cancer Institute; Publication dated Jun. 4, 1991 entitled CEA (Carcinoembryonic Antigen)

National Cancer Institute; Cancer of the Prostate Research Report

WO 9201809; Authors Gross R. L.; Usinger W. R.

Levels of myc Protein, . . . ; International Journal of Cancer; Volume 43, 1989

Stopping the Crab; Author: Peter Radetsky; Discover Magazine, Volume 13, Page 32, March, 1992

Journal Article in Index Medicus; entitled Simultaneous Assessment of Chromatine Structure . . . ; Stokke, et al. Vol. 44; Cancer Research; Cellular DNA; November, 1984

The most relevant of the patented prior art uncovered is the Canadian Patent No. 1 200 477 issued Feb. 11, 1986 which pertains to a method for detecting luminescence in living cell systems. The method of said patent pertains to the utilization of a luminescent dye combined with a living cell and a time dependent study in the change of luminescence in polarized light. This method is based upon previous work of Cercek utilizing blood and lymphocyte cells isolated from blood and then mixed with dyes.

The method described in Canadian Patent No. 1 200 477 is entirely different from the present invention since it does not utilize whole blood and it does not utilize the same method or procedures. The method of Canadian Patent 1 200 477 is subject to a number of problems in handling, treating, filtering and working with the blood and the dying of blood and tissues. Said method of the Canadian Patent is rather complicated because it needs the special preparation of blood cells and the special construction of a polarization fluorimeter. Most importantly, Canadian Patent No. 1 200477 does not provide a basis for early cancer detection.

Other relevant prior art pertains to the detection and analysis of CEA Carcinoembryonic antigen in blood. The National Cancer Institute publication indicates CEA is one of a number of tumor markers that have been studied by the National Cancer Institute. CEA has not been recommended as a screening test to detect cancer in people without the symptoms of the disease because the CEA assay was determined to not be specific enough to differentiate between cancer and other health problems.

The next relevant prior art uncovered is the National Cancer Institute publication on Cancer of the Prostate which in pages 8 and 9 discusses the laboratory test including the identification of other tumor markers such as prostatic acid phosphatase and its concentration in blood. This test is very specific with respect to cancer of the prostate and in particular to the metastatic stage of the disease. Furthermore, this test is not entirely reliable because elevated levels of prostatic acid phosphatase can be observed in men with a non-cancerous disease and prostatic acid phosphatase is not always seen in those with prostatic cancer. Similarly, in the same publication, serum prostate specific antigen (PSA) is another antigen found in the blood. PSA is used not as a diagnosis but instead as a test for determining the stage of the prostate cancer, as well as the patient's response to treatment.

Other prior art (WO 9201809) pertains to the combination of sample lymphocytes and red blood cells to effect spontaneous rosette formation. The rosette formation is determined by light scatter analysis.

Prior art such as the article in the Discovery Magazine is relevant to the study of genes and particularly to the absence of a gene whose absence triggers metastasis which pertains to the spread of tumors through the blood. This analysis apparently pertains to a test for tumors but only once an advanced stage has been reached wherein the blood becomes a vehicle for the spread of the tumors.

Prior art such as the Journal Article in Index Medicus by Stocke, et al pertains to measurements utilizing wavelength and fluorescence of light scatter in cells stained with 7-AMD. This prior art studies the proliferation of cells similar to that described in the International Journal of Cancer.

Other approaches of examining blood serum at molecular level use ESS-spectroscopy (also known as Electroparamagnetic Resonance Spectrography) or NMR-Relaxation (Nuclear Magnetic Resonance). These methods employ the measurements of time variable values of NMR relaxation or the measurements of ESS spectrum after a serum has already been exposed to ultrasound or after some chemical agents have been added thereto in order to diagnose a patient's body condition by the set of parameters so obtained. The shortcoming of such methods is that they are complicated as they require either preliminary exposure to external fields or the addition of various reagents to the serum. Furthermore, a considerable amount of plasma is required, this being no less than 3 to 4 cm3 of venal blood. In addition, such methods require the development costly test setups such as NMR equipment. Thus, such approaches do not meet the principal objectives of the method of the invention which are to create a low-cost and rather simple but at the same time reliable and efficient method for diagnosing oncological diseases which does not require a considerable amount of blood for performing the analysis nor require the development of complicated and costly test setup equipment.

The general methods of diagnosing oncological diseases by way of X-ray examination, biochemical testing of blood, morphological and citological examinations, as well as detection of atypical and anomalous cell forms are well known.

Such methods are rather laborious, requiring repeated and prolonged tests and not efficient at the early stages of a disease. They are also nor practical for mass screening. As an example, the most reliable of these methods, computer tomography, costs app. $1 million for the main instrument and takes over 30 minutes to examine one person at a high cost. In contrast, the method of the invention is simple, inexpensive and the analysis takes less than 10 minutes with experienced staff.

As late as Mar. 15, 1993, U.S. News and World Report, in an article entitled "The Breast Cancer Scare", concludes with the remarks (extracts follow from the closing paragraphs) . . . "A surgeon would use a needle to suck cells out of the lump, a quick non-surgical procedure in which the surrounding skin is numbed. Even if cancer cells are absent, the lump could still be malignant . . . (citing Harvard Medical School's assistant Professor of Surgery), "The most important factor in deciding whether to do a biopsy is physician judgment, and that is very difficult to measure". The closing paragraph states, "Some day, a simple blood test might predict who is headed toward breast cancer and who can lower her vigilance. For now, women under 40 can take comfort in knowing that their youth is their best defense" (End of Article).

The method of the invention is indeed the hoped-for simple blood test mentioned in the above paragraph and not only does it pertain to breast cancer, but to all types of oncological diseases, without limits on gender, or age.

As a result of reviewing searched and known prior art, it is believed none of the known prior art suggest the present invention.

OBJECTS OF THE INVENTION

It is among the objects of this invention to create a physical method for the early diagnosis of oncological diseases through molecular level analysis.

It is also an object of the invention to provide a low cost alternative for diagnosing the presence of oncological disease, especially in comparison to the expensive current procedures used for diagnosing cancers, such as biopsies, tomography, exploratory surgery, X-ray series and endoscopy.

Another object of the invention is to provide a quick method for diagnosing the presence of oncological diseases, requiring less than 10 minutes for a diagnosis.

Yet another object of the invention is to provide a simple method for diagnosing the presence of oncological diseases, which is simple for the person conducting the test, as well as for the test subject.

A further object of the invention is to provide a method for diagnosing the presence of oncological disease that facilitates mass screening.

Another object of the invention is to provide a method for diagnosing the presence of oncological diseases that is reliable and effective.

An objective of the invention is to provide a method for diagnosing the presence of oncological diseases that eliminates the need for complicated apparatus.

An additional objective of the invention is to provide a method for diagnosing the presence of oncological disease that requires only a small blood sample which may be obtained from the finger of a test subject. Typically, amounts of blood as small as 0.05 to 0.4 ml or about 1 drop to about 10 drops may be used, as well as blood obtained from other sources, such as the vein, which may be obtained as part of blood obtained for other medical tests.

Another objective of the invention is to provide a method for diagnosing the presence or absence of oncological diseases that is conducive to encouraging most people, who are reticent to undergo routine or preventive conventional tests, to submit to a simpler, faster and cheaper test.

SUMMARY OF THE INVENTION

This invention pertains to a method for diagnosing the presence or absence of oncological diseases wherein an effective small amount of blood is obtained, such as from a finger, and a solution containing blood plasma or serum is exposed to laser radiation and the values of one or more parameters are determined upon measurements at molecular level. Said parameters are then compared with analogous measured or established parameters of a reference solution to determine whether there are significant variations or similarities that indicate the absence or presence of oncological diseases or a predisposition to same.

In a preferred embodiment of the invention, blood plasma or serum is diluted in water up to 25% of the volume and the solution is then exposed to laser radiation in the standard mode (meaning the normal operating range the laser is designed for, such as mode TEMoo used in conjunction with a Helium Neon laser). Measurements and determinations are then made of the coefficient of Rayleigh light scattering "R" in the solution and other indicative parameters such as the effective mass "M" and a parameter of molecular interaction "B" of scattered particles in the solution. The values of R, M and B are then compared with respective reference indicative parameters $R_{ref}$, $M_{ref}$ and $B_{ref}$ of a reference solution, such as one obtained from the blood serum of healthy individuals. If $R/R_{ref} > 2$, $M > M_{ref}$ and $B < B_{ref}$, then an oncological disease is diagnosed as a fact.

Alternately, for a quick risk assessment, one or more of the values of said indicative parameters are compared against known and established ranges of values of said parameters in individuals that have proven oncological diseases. Depending on where the values of the parameters fall, a quick assessment is made as to whether further testing is required or whether further tesing is not warranted for a period of time.

The method of the invention is a simple, essentially two step process. It is simple for the subject and the person performing the test. It uses simple lab equipment and is quick (less than 10 minutes only) and is, therefore, less expensive to perform. It is suitable for mass screening because of its simplicity, low cost and the short time it takes to complete the diagnosis. The method is also reliable and effective because there are clear demarcation ranges between the parameters determined in the method of the invention for healthy persons and those with oncological diseases.

Besides the inherently low cost of the method of the invention, the simple procedure of the method of the invention does not require test subjects to undergo traumatic experiences or procedures that often induce apprehension, such as procedures involving invasive techniques, procedures requiring large amounts of venal blood, biopsy acquisition of body tissue through surgical procedures, other procedures requiring the undergoing of a close physical examination, procedures requiring exposure to radiation, and procedures where subjects are confronted with sometimes claustrophobically overwhelming apparatus.

The simplicity and non-traumatic nature of the method of the invention can encourage millions of people to take the simple test of the invention, thereby saving millions of lives world-wide through early diagnosis.

BRIEF DESCRIPTION OF DRAWINGS

The features and description of the invention will become more apparent in conjunction with the following figures wherein:

FIG. 2 is an illustrative sample table comparing the values of indicative parameters $R/R_{ref}$, M and B for patients with oncological diseases with respect to healthy individuals.

FIG. 7 provides a sample test apparatus group for more precise and greater than 3 indicative parameter measurements and determinations.

DETAILED DESCRIPTION OF THE PREFERRED EMBODIMENTS

Figure 1:
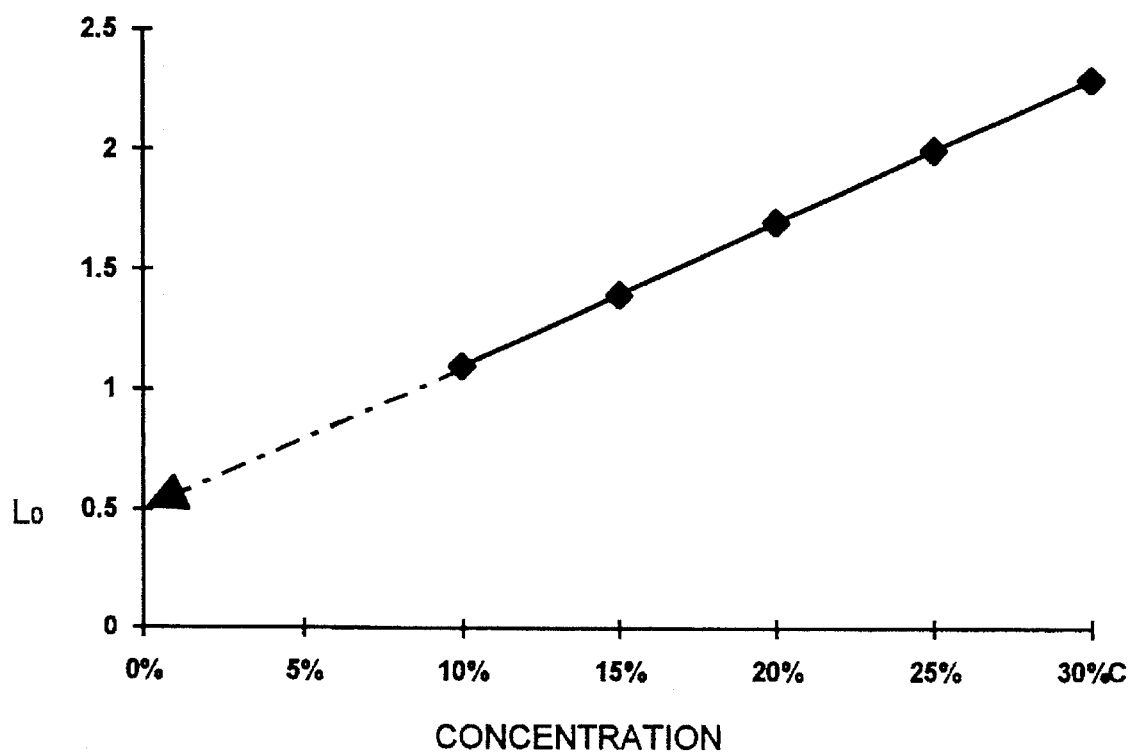
FIG. 1 is a graph illustrating the dependency of the complex CH/R with respect to C (concentration).

The method of the invention is advantageous in many respects including the fact that it provides a reliable and effective method for the diagnosis of oncological disease, without requiring a considerable amount of blood or complicated and expensive equipment. Furthermore, the method of the invention does not require preliminary processing of blood plasma or serum or require prolonged measurements. The invention efficiently allows the distinction of healthy groups of people from those who have oncological diseases, as well as those prone to oncological diseases.

More specifically, the method of the invention for diagnosing oncological disease does not require preliminary exposure of either blood plasma or blood serum to external fields nor the involvement of chemical agents. The method and its related apparatus makes it unnecessary to obtain a great deal of blood from a test subject and it is sufficient to use a small, effective amount of blood, such as from a finger. Such amounts of blood may be 1 to 10 drops or about 0.05 ml to 0.4 ml from which red blood cells are preferably removed to obtain blood plasma. Blood serum, which is used herein, may also be used and refers to blood plasma from which the clotting factor has been removed. Expensive equipment is not required and analysis can be made with the aid of laboratory apparatus that facilitates the measurements, such as a laboratory nephelometer, (such as that supplied by Malvern Instruments Ltd. in Worcestershire, in the United Kingdom). Most importantly, the method of the invention is characterized by high reliability and efficiency because a diagnosis can be made on the basis of several parameters measured on the molecular level. The measurement is most effective when blood plasma or blood serum is used as better analysis of the scattering is realized.

The method of the invention entails the examination of the physical parameters of blood plasma or serum at a molecular level. It is a method for determining the presence or absence of oncological diseases wherein a solution containing a small amount of blood plasma or serum is exposed to laser radiation and the values of one or more parameters are determined upon measurements at molecular level. Said parameters are then compared with analogous measured parameters of a standard or reference solution to determine whether there are significant variations or similarities that indicate the absence or presence of oncological diseases or a predisposition to same. Alternately, the parameters obtained through the test method of the invention are compared against known established reference values.

In a preferred embodiment of the invention blood plasma or serum is diluted in distilled water with a concentration of up to 25% in volume. The solution thus obtained is exposed to laser radiation in standard mode (meaning the normal operating range the laser is designed for, such as mode TEMoo used in conjunction with a Helium Neon laser) and the Rayleigh light scattering factor R in the solution is measured. A suitable laboratory apparatus is utilized for the analysis, such as a laser laboratory nephelometer. Upon also determining the effective mass parameter M and parameter of intermolecular interaction B of the serum particles being scattered, the values of R, M and B are then compared with the analogous parameters of a standard or reference solution selected earlier and if the values $R/R_{ref}>2$, $M>M_{ref}$ and $B<B_{ref}$, oncological disease is diagnosed. The average time for analysis by experienced staff is less than 10 minutes and automating the process will reduce this time further.

Other objects and features of the invention will become more apparent as this description proceeds, especially when taken in conjunction with the details of the accompanying figures.

FIG. 1 is a graph where the dependency of the complex CH/R with respect to C is shown— that is, L or $CH/R_\theta \equiv f(C)$, where H is a constant value determined by the characteristics of the diagnosing instrument (wavelength of the light source) and by an index of the refraction of the solution (blood serum) and where C is the concentration of the Rayleigh light scattering of the solution and R is a coefficient of the Rayleigh light scattering of the plasma solution. The line is almost linear. The extrapolated intersection of the line with the ordinate axis $L_0$ (as C→0 concentration on the horizontal axis) is used to determine the effective mass M of scattered particles in the solution. The slope of the line is used to determine the parameter B of molecular interaction. C for the abscissa or horizontal axis, is shown expressed in %, since this better illustrates concentration. In calculations, however, decimal values are utilized in lieu of percent as they represent the actual ratios of dilution ( example 25% is 0.25 and 15% is 0.15). L can be measured in mole/grams.

FIG. 2 is an illustrative sample table comparing the values of indicative parameters $R/R_{ref}$, M and B for patients with oncological diseases with respect to healthy individuals. This sample table illustrates that an oncological condition is indicated when $R/Rref>2$, $M>M_{ref}$ and $B<B_{ref}$ when three parameters are used for the test. The table also illustrates the clear differences in indicative parameter values for healthy individuals and oncological patients. As an example, Test Subject No. 4 in the table of FIG. 2 is 27 years old, is apparently healthy and has no complaints. Clinical examinations of blood and urine are normal. Biochemical blood test indicated total protein of 8.7% and an A/G Index (Albumin/Globulin Index) of 2.02. The three parameter test resulted in indicative parameter values of $R/R_{ref}=1.1$; $M=18.5\times10^4$ and $B=400\times10-4$. Subject is diagnosed to be free of oncological disease as the indicative parameter values in this case fall in the range for subjects free of oncological disease and fall out of the range for patients with oncological disease.

Figures 3A, 3B:
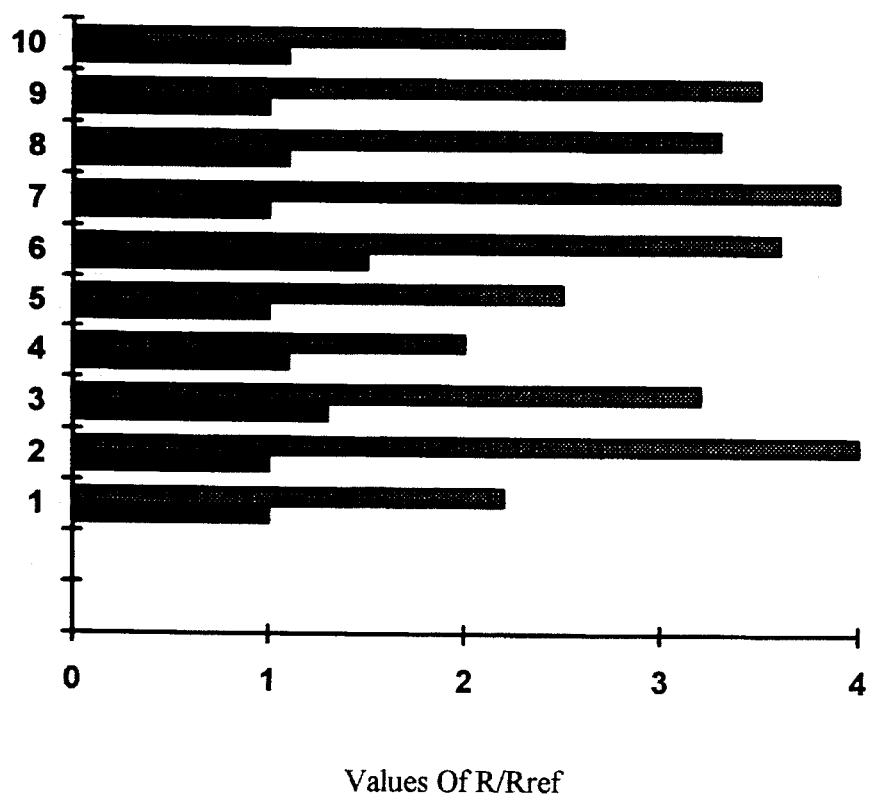
FIG. 3A and 3B includes a portion of the sample table of FIG. 2, with a specific visual (bar graph) comparison of sample $R/R_{ref}$ indicative parameters for patients with oncological diseases with respect to healthy individuals.

FIG. 3A and FIG. 3B include a portion of the sample table of FIG. 2, with a specific visual (bar graph) comparison of sample $R/R_{ref}$ indicative parameters for patients with oncological diseases with respect to healthy individuals. In this chart, the vertical axis numbers represent the sample test numbers, whereas the horizontal or abscissa axis numbers represent the values of indicative parameter $R/R_{ref}$. The shorter bars represent the values of $R/R_{ref}$ for healthy individuals, whereas the longer bars represent the values of this parameter for oncological patients. It can be easily noted that there is a significant difference in the values of this indicative parameter for oncological patients versus healthy individuals.

Figures 4A, 4B:
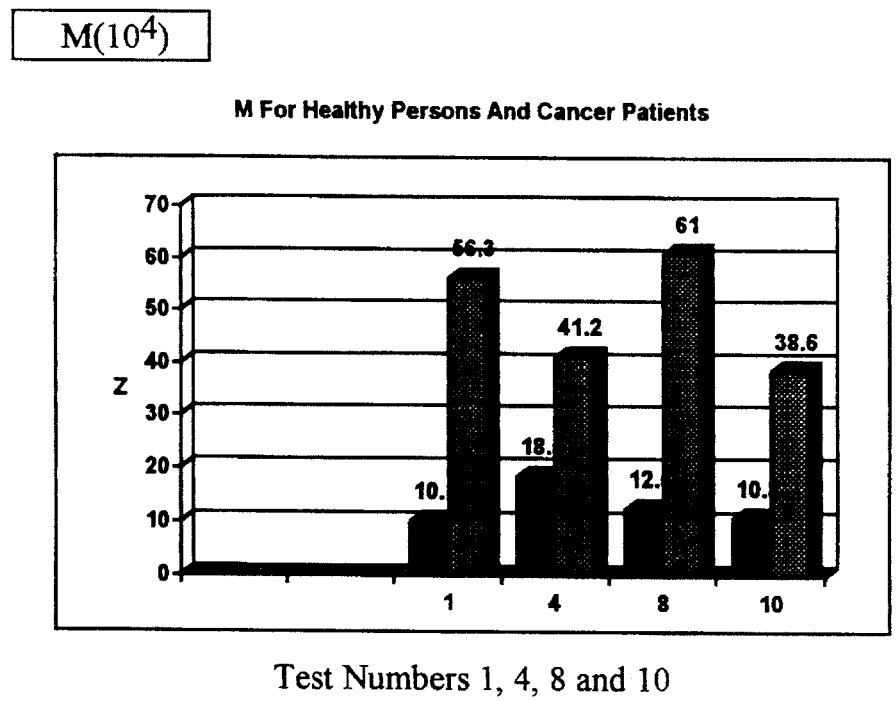
FIG. 4A and 4B includes a portion of the sample table of FIG. 2, with a specific visual (column chart) comparison of sample M indicative parameters for patients with oncological diseases with respect to healthy individuals.

FIG. 4A and FIG. 4B include a portion of the sample table of FIG. 2, with a specific visual (column chart) comparison of sample M indicative parameters for patients with oncological diseases with respect to healthy individuals. The numbers on the horizontal or abscissa axis represent the four sample tests, whereas the numbers on the ordinate or vertical axis represent the values of indicative parameter M. In this figure, the larger values and therefore the larger columns correspond to the values of parameter M for oncological patients, whereas the shorter columns represent the values of parameter M for healthy individuals. It is easy to note the large difference in the values of parameter M for oncological patients versus healthy individuals. M can be measured in grams/mole.

Figures 5A, 5B:
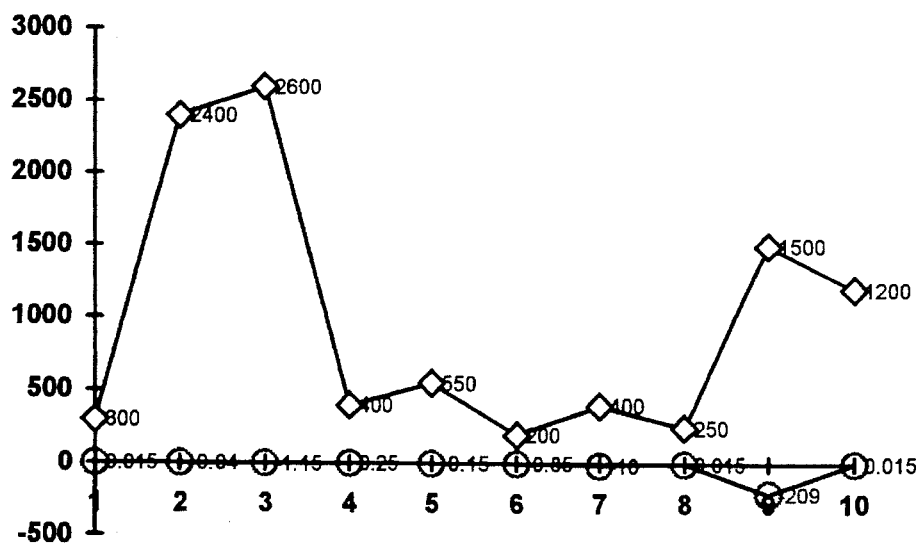
FIG. 5A and 5B includes a portion of the sample table of FIG. 2, with a specific visual (line graph) comparison of sample B indicative parameters for patients with oncological diseases with respect to healthy individuals.

FIG. 5A and FIG. 5B include a portion of the sample table of FIG. 2, with a specific visual (line graph) comparison of sample B indicative parameters for patients with oncological diseases with respect to healthy individuals. The values for indicative parameter B for oncological patients have a range of +0.25 to −209 ($\times10^{-6}$) in the sample table, whereas the values of B for non-oncological individuals is in the range of +200 to +2600 ($\times10^{-6}$). Accordingly, the traced curve connecting the values of indicative parameter B for oncological patients is very close to the horizontal or abscissa axis because of the large difference in the scale and ranges. The vertical ordinate axis represents the values of parameter B. The legend 1 to 10 below the horizontal axis represents the sample test numbers. It is obvious that there is a large difference in the values of parameter B for oncological patients versus healthy individuals. B can be measured in $mole.cm^3/g^2$.

Figure 6:
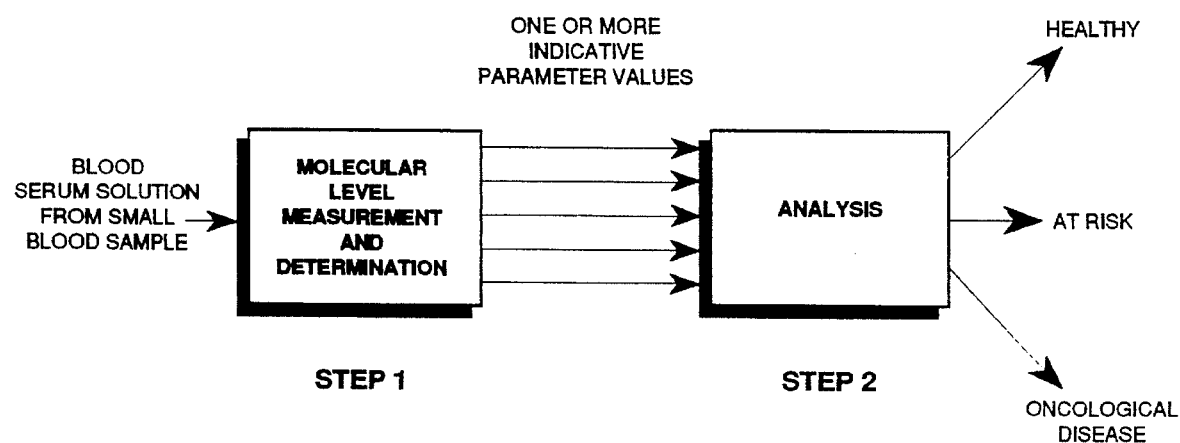
FIG. 6 depicts the process of the basic method of the invention essentially consisting of a two step process.

FIG. 6 depicts the process of the basic method of the invention, essentially consisting of a two step process of a) exposing a blood serum solution to laser radiation in a suitable apparatus for making molecular level measurements and determinations of indicative parameters and b) analyzing the indicative parameters to obtain a diagnosis with respect to the presence or absence of oncological disease.

FIG. 7 provides a sample test apparatus group comprising a list of items making up one type of apparatus group for more precise measurements and determinations and facilitating imaging associated with indicative parameters. The electrophoresis kit can be of the Malvern (U.K.) type or equivalent.

The following additional discussions will further disclose and clarify the theoretical and practical aspects of the method of the invention.

The Rayleigh light scattering phenomenon appears when the medium is exposed to electromagnetic radiation. Under the influence of such radiation, the oscillations of electrical charges (oscillating dipoles) appear in the scattering particles (molecules) which are distributed in the medium at random and such charges become the source of the electromagnetic radiation with the same frequency as the incidence radiation and are called the scattering radiation. Intensity $I_R$ is the experimentally determined measure of light energy.

The scattering coefficient (the so called Rayleigh Factor) is determined by:

$$R_\theta = r^2 I_R / I_o \qquad (1)$$

where θ is the angle between the scattered and incidence beams and where r is the distance from the scattered volume to a point of observation and where $I_o$ is the intensity of the incidence radiation that can be measured in millivolts and $I_R$ is the intensity of the scattered radiation, such as at 90°, that can also be measured in millivolts.

$R_\theta$ can be obtained in relative units for a given apparatus. To calculate $R_\theta$ in absolute units (for example in $cm^{-1}$), measurement is made of the intensity of light in a well known compound, such as benzene $C_6H_6$, at preestablished conditions (cuvette, wavelength of the laser, the distance r and incident intensity $I_o$). In this case $R_\theta$ for a given solution such as blood plasma is expressed by:

$$R_\theta = I_{Rs}/I_{Rb} \times R_{\theta b}(n_w/n_b)^2 \qquad (2)$$

In equation (2) above, $\theta$ is the angle between the scattered and incidence beams such as 90°; $I_{Rs}$ is the intensity of the scattered radiation in blood serum from the above determined range, $I_{Rb}$ is the intensity of the scattered radiation in benzene, $n_w$ and $n_b$ represent the refractive index respectively, in water and benzene; $R_\theta$ is the Rayleigh Factor for blood serum being determined.

To illustrate the practical application of the above equation to determine a desired $R_\theta$ using a reference $R_{\theta ref}$, such as $R_{\theta b}$, experimental values can be used as a reference. As an example, the experimental data of the absolute value of R at $\theta=90°$ or $R_{90°}$ in $C_6H_6$ and for a radiation source wavelength $\lambda=546$ nm $\cong 15.10^{-6}$ cm$^{-1}$ (ref. D. J. Coumou, J. Colloid Science, 15, 498, 1960). As another example, for $\lambda=632.8$ nm and $C_6H_6$, $R_{90°} \cong 13.10^{-6}$ cm$^{-1}$. Also, the respective characteristic value of $I_{Rb}$ for $C_6H_6$ during various experiments has been in the range of 20–30, with a respective characteristic value of intensity $I_{Rb}$ for blood serum sample in the range of 200–400. From the aforementioned and, using equation (2), the absolute value of the Rayleigh Factor for a given concentration of blood serum can be determined by substitution (in this case using the reference value of $R_\theta$ for $\lambda=632.8$ nm: $R_{90°}=200/20\times 13.10^{-6}$ $(n_w/n_b)^2 \cong 100.10^{-6}=10^{-5}$ cm$^{-1}$ ($n_w$ and $n_b$ each representing the refractive index, $n_w=1.32$ and $n_b=1.5$ respectively, in water and benzene).

The Rayleigh Factor is also determined by the mass of scattered particles, concentration of particles in solution, as well as by a coefficient characterizing the energy of particle of interaction, expressed by:

$$R_\theta = CH/(1/M+2BC) \qquad (3)$$

where C is the concentration of particles (macromolecules) in the solution and where M is the mass of the particles and where B is the coefficient of intermolecular interaction and where H is the so called Debye's Constant of the solution. Also:

$$H=2\pi^2 n_o^2 (dn/dc)^2/\lambda^4 N_A \qquad (4)$$

where $\lambda$ is the wavelength of incidence radiation (laser), where $n_o$ is the refractive index of a suitable solvent, such as distilled water, (as an example $n_o=1.32$ in the instance of distilled water and an example wavelength $\lambda=632.8$ nm), where $N_A$ is the Avogadro Number being equal to $6.0221367\times 10^{23}$ 1/mole, and where dn/dc is the refraction index increment of the solution. dn/dc can be determined with the help of a refractometer for two or three solution concentrations and actually it always linearly depends on the concentration. H can be measured in cm$^2$ mole/g$^2$.

As an illustration of calculating H, the preceding values of $n_o=1.32$, $\lambda=632.8$ nm, $\pi=3.1416$, $N_A=6.02\times 10^{23}$ together with the experimental value of $d_n/d_c=0.336$ are substituted in equation (4). Thus $H=2\times(3.1416)^2\times(1.32)^2\times(0.336)^2$ divided by $(6.328\times 10^{-5})^4\times(6.02\times 10^{23})=4.02\times 10^{-7}$.

The exact process of the preferred embodiment is realized in the following manner: A syringe/measuring pipette is used to add to the distilled water contained in an ampoule or a small glass cuvette such amount of blood plasma or serum that its concentration in the solution does not exceed 25% in volume. With higher concentrations of the solution, the light scattering is excessive because a multiple scattering effect appears and it considerably hampers an interpretation of the results. The solution thus obtained is then exposed to laser radiation (for example, He—Ne laser in the standard mode).

The measurements and defining the Rayleigh light scattering parameters in the solutions of various concentrations are performed as follows: Intensity of the scattered radiation $I_R$ in millivolts in the solution is measured at an angle of 90° to the incidence beam then the scattering intensity is measured in the reference sample ($I_{ref}$). A scattering factor value $R_\theta = I_R/I_{ref}$ is determined by comparing the scattering intensity in the blood plasma or serum solution of the given concentration with the scattering intensity in the reference sample.

Parameter H is calculated for the given wavelength of exciting light $\lambda$ and given value of (dn/dc). Thereafter, the complex $CH/R_{90°}=L$ is plotted as a function of the blood plasma or serum solution concentration (See FIG. 1). Using a linear extrapolation of this dependency (the line obtained in the plotted graph) for a zero concentration (C→0), a point on the ordinate axis ($L_o$) is determined and it allows finding an average effective mass parameter M of scattered particles in the solution and, by the inclination (slope) of dependency, the parameter of intermolecular interaction B is determined.

To further illustrate the method of determination of parameter M, reference is made to the dependency of L (in FIG. 1) to $CH/R_\theta$. Substituting now expression (3) for the $R_\theta$ in the denominator of complex $CH/R_\theta$, we derive that L can be expressed by $CH \div CH/(1/M+2CB)$, which simplifies to L being expressed by $1/M+2CB$. As C→0, this reduces to L being expressed by $1/M$. If then L is expressed by $1/M$, then M can be expressed by $1/L$. Looking now to FIG. 1 as an illustration, the ordinate axis intercept point for L, or $L_o$, is $0.5\times 10^{-5}$ and therefore 1/L, that is M, is $1/0.5\times 10^{-5}$ or $20\times 10^4$.

As for an illustration of determining parameter B through the slope of the plotted line L as in FIG. 1, $\Delta L/\Delta C$ is the slope or differential of line L, and as a differential, is mathematically more commonly expressed as $\delta L/\delta C$. Differentiating the above derived expression $1/M+2CB$ for a given numeric value of M, $\epsilon L/\epsilon C=2$ B. Thus, obtaining the change in ordinate $\Delta L$ and a corresponding change in the abscissa $\Delta C$ and using $\Delta L/\Delta C=2B$, the value of B can be determined. As a practical illustration, referring to FIG. 1, $\Delta L$ at C=0.15 and C=0 is: $1.5\times 10^{-5}$ minus $0.5\times 10^{-5}$ which equals $1\times 10^{-5}$. Corresponding to this $\Delta C$ is a difference of 0.15. Accordingly $\Delta L/\Delta C=1\times 10^{-5}/0.15=6.67\times 10^{-5}=2B$ and $\therefore B=6.67\times 10^{-5}/2=3.33\times 10^{-5}$.

The obtained parameters R, M and B are compared with the analogous preestablished or newly determined reference parameters $R_{ref}$, $M_{ref}$ and $B_{ref}$ of a reference blood serum solution from a healthy person (from tests on a reference solution). An oncological disease is diagnosed if $R/R_{ref}>2$, $M>M_{ref}$ and $B<B_{ref}$. This is illustrated in FIGS. 2, 3A, 3B, 4A, 4B, 5A and 5B.

The scattering properties of blood plasma and serum are determined by physical parameters of molecules dissolved in it, as well as by physical-chemical processes going on in the plasma.

Protein macromolecules forming a part of the blood plasma (serum), mainly albumin and globulin, carry electrical charges on their surfaces, the potential and polarity of which influence the character of molecular interaction of protein molecules.

The inventors have observed and confirmed that the occurrence of oncological disease or a predisposition to it results in changes of said surface charges on the protein molecules. With the decrease of surface charge, the Coulomb repulsive forces between the molecules also decrease and, owing to the attractive forces, the molecules start to associate together, forming clusters. The mass of scattering particles in the solution increases and correspondingly the coefficient of R also increases.

The examinations of blood serum solutions carried out during tests have shown the factor R to be two and even higher times more in the blood serum of patients with oncological diseases, as compared to healthy individuals. This is shown in FIG. 2 in the sample table which is based on a 25% concentration of blood plasma or serum solution.

Blood plasma or serum consists of protein with different mass and in various proportions. In the method of the invention, only the effective mass of proteins in blood plasma is measured. In case of oncological disease, this effective mass definitely increases as shown in FIG. 2 in the sample table and more clearly and visually in FIGS. 4A and 4B.

For the reference solution, this being the blood serum of an obviously healthy person, the parameter B is equal to $5.10^{-3}$ (mole/g). For the plasma or serum of blood from oncological patients, the parameter B is considerably less ($10^{-7}$ to $10^{-8}$) and in a number of cases, B even has a negative value. This is illustrated in FIG. 2 in the sample table and more clearly and visually in FIGS. 5A and 5B. The shift in sign is explained by a change of the intermolecular interaction potential sign when a surface charge on a protein changes.

As is seen from the sample table of FIG. 2, the absence of overlapping in R, M and B values for a healthy person versus oncological patients testifies to the fact that the proposed method of diagnosing oncological diseases is reliable and effective. FIGS. 3A, 3B, 4A, 4B, 5A and 5B further provide a visual comparison of indicative parameters $R/R_{ref}$, M and B in healthy persons and patients with oncological disease.

The following will further illustrate the basis for various possible diagnostic approaches and related medical considerations employing the general method of the invention or its embodiments for determining the presence or absence of oncological disease, as well as for determining individuals "at risk".

The conditions of various organs, tissues and blood of a human organism is characterized or reflected by an appropriate sets of parameters as determined by instruments and analytical methods.

The value of the ranges for these parameters that correspond to apparently healthy individuals or individuals with health problems are determined by a statistical analysis derived from various biological and biochemical models. This is indeed common and accepted in many types of medical tests such as in the common Blood checks performed where the normal or abnormal ranges for cholesterol, blood sugar, etc. are derived from statistically pre-established values.

It would thus be appropriate to establish values of parameters in the course of statistical analysis of the relative health status of individuals (based on the compliance of the condition of their organs, performance of physiological functions, etc.), relative to models, or the statistical values obtained for individuals with parameters that reflect the condition of their organs, performance of physiological functions and other relevant parameters.

Based on this reasoning, the values of parameters $R/R_{ref}$, M, B derived through the preferred embodiment method of the invention have been statistically and relatively established for "healthy persons". These values have been established on the basis of the theoretical (biochemical) considerations pertaining to the biological functions performed by blood plasma, as well as on the basis of statistical data following the examination of about 450 healthy persons of 18–20 years of age (GM University of Moscow Gov.) students. The data about the general condition of their health had been provided by the MGU Clinic where they undergo general medical examination. Similarly, many tests have been carried out separately in relation with the method of the invention on other individuals that were undergoing various other tests and procedures.

The parameters R/Rref, M and B for healthy persons and those definitively diagnosed as having oncological disease (prior to treatment), greatly differ.

Typical parameters of the "healthiest" persons are $R/R_{ref}=1$; $M=200,000$ and $B=10 \times 10^{-4}$ to $10 \times 10^{-3}$.

Typical parameters of oncological patients at advanced stages of disease (prior to treatment) are $R/R_{ref}>4$, $M>800,000$ and B ranges from $+10 \times 10^{-6}$ to $-10 \times 10^{-6}$.

Indicative parameter values falling closer to those of "healthiest" persons and those falling closer to values expected of individuals with oncological disease, provide an indication of the degree of risk or deviation from established or newly derived references. The range within which the parameters for the group of individuals at risk fall, is characterized by statistics, as a result of examinations. With an increase in the number of individuals undergoing the test, the risk group range can be narrowed. Using multiple sample references can establish a range of reference values and further help in comparisons where it is desired to determine whether the test subject's indicative parameter values fall inside or outside a preestablished reference range.

The method of the preferred embodiment of the invention is thus a rapid three parameter test for diagnosing cancer diseases since it only requires less than 10 minutes to make the test. Furthermore, the test method of the invention is simple, not very costly, reliable, effective and impartial. As explained or illustrated earlier, the values of the indicative parameters in the preferred embodiment of the invention can be determined with the help of apparatus and manual calculations and plotting, or combinations of measuring, calculating and plotting apparatus.

As an illustration, referring to the example of the 27 year old test subject mentioned under a description of FIG. 2, the subject sumbitted to the test apparently healthy with no complaints. Clinical examinations of blood and urine were normal. A blood sample from the finger was obtained and centrifuged to seperate plasma. Using three concentrations in the solution consisting of plasma and distilled water, readings were taken with a nephelometer of R and the parameters of M and B determined as $R/R_{ref}=1.1$; $M=18.5 \times 10^4$ and $B=400 \times 10^{-4}$ using manual plotting and a scientific calculator. Subject is diagnosed to be free of oncological disease as the indicative parameter values in this case fall in the range for subjects free of oncological disease and fall out of the range for patients with oncological disease.

It is the belief of the inventors that this simple and effective method of diagnosing oncological disease can find a wide application in clinical practice, especially when a possibility of the disease is suspected or when various factors indicate a preference for screening (such as hereditary factors) and exposure to hazardous material. The rapid tests can be applied on a large scale with respect to groups that occupationally or environmentally are at risk, or when prophylactic or preventive examinations are carried out. The method of the invention is also very well suited to becoming a part of an annual or routine blood test, because only a minute amount of blood is required and the test is easily and rapidly carried out.

Other specific methods employing the same molecular level analysis principles with similar or related indicative body fluids, such as whole blood, its other constituents and urine, using some variations of the test or instrumentation, are all deemed to be within the scope and spirit of the invention. Such methods can be applied wherever additional precision or analysis is desired, such as for individuals for whom the mentioned indicative parameters fall in the borderline portion of the ranges expected for those with oncological disease. For example, to achieve the additional precision or additional diagnostic insight within the scope and spirit of the invention for such presumably at-risk individuals, suitable precision instrumentation, such as photon correlators (such as from Malvern in U.K.) may be utilized together with additional indicative parameters, such as parameters related to Brownian Motion.

Such a setup is disclosed in FIG. 7 for one type of a group of apparatus representing another embodiment of the invention. In this embodiment, within the scope and spirit of the invention, indicative parameters are first determined and again referenced and analyzed against references or established standards, however, in this embodiment employing a variation of the referencing analysis. In this embodiment, a multidimensional functional image of the test sample blood plasma is plotted on the basis of the known functional relationships between the indicative parameters. The shift in direction of the analogous multidimensional functional image of known oncological patients is then established as a reference axis. The multidimensional image of the first mentioned or test sample that is to be analyzed is then projected against the reference axis. The shift of the test sample image along the reference axis is then noted to diagnose the condition of the test subject and where the shift towards the oncological reference occurs, presence of oncological disease is diagnosed. Thus, this embodiment employs a variation in the analysis step to yield a characteristic shift type indication along a reference axis. As more parameters are utilized, the more complex functional interrelational images produced by additional parameters can conceivably yield valuable characteristic shifts along the reference axis, especially when the analogous reference images of specific types of oncological and other diseases are employed as reference axises. For the process of this embodiment of the invention, many types of suitable plotting and imaging software that are readily available on the market can be utilized (such as Global Lab 2.0 from Data Translation, Marlboro, Mass.) together with the set-up disclosed in FIG. 7, to further facilitate and automate the plotting, imaging and comparison process. Inherently, characteristic shifts along analogous known reference axises for specific types of oncological diseases can be helpful in identifying the type of the oncological disease. Except for the cost of the instrumentation which would be more expensive, this embodiment would still provide all the advantages of the basic method of the invention plus the additional capabilities and applications mentioned. An approach utilizing the method of this embodiment may be helpful in analyzing other types of disease at a molecular level.

It is sincerely hoped that the carnage wreaked by oncological diseases is greatly reduced through providing a method through this invention that is conducive to routine or mass screening, thereby providing a means for early diagnosis and the enhancement of survival rates.

We claim as our invention:

1. A method for screening for the presence of oncological diseases of the stomach, uterus, cervix, breast and throat comprising:
   (a) obtaining an effective amount of about 0.05 ml to 0.4 ml of a blood sample untreated except for anticoagulants in the form of an indicative solution of blood constituents;
   (b) exposing said indicative solution of blood constituents to laser radiation to cause scattered radiation from said indicative solution;
   (c) measuring surface charges on protein molecules as scattered radiation and determining parameters of effective mass M and molecular interaction B for said indicative solution at a molecular level;
   (d) comparing said measured and determined parameters of said indicative solution with analogous parameters of established reference range standards;
   (e) screening for the presence of oncological disease of the stomach, uterus, cervix, breast and throat based upon a comparison of said measured and determined parameters of said indicative solution with said established reference range standards.

2. The method of claim 1 wherein said indicative solution of blood constituents is blood plasma.

3. The method of claim 1 wherein said indicative solution of blood constituents is blood serum.

4. The method of claim 1 wherein said established reference range standards is a group of reference values.

5. The method of claim 1 wherein said established reference range standards is a group of reference solutions.

6. The method of claim 1 wherein said step of measuring surface charges on said protein molecules is measured as a coefficient of Rayleigh light scattering "R" of said indicative solution.

7. The method of claim 1 wherein said parameter of effective mass M of blood constituent molecular protein molecules scattered is measured from said indicative solution.

8. The method of claim 1 wherein said parameter of molecular interaction B is measured from said indicative solution.

9. The method of claim 1 wherein said effective amount of untreated blood is obtained from a finger.

10. The method of claim 1 wherein said effective amount of untreated blood is obtained as a portion of a blood sample from another blood analysis.

11. The method of claim 2 wherein said blood plasma is diluted in a medium for facilitating said step of measuring surface charges on said protein molecules.

12. The method of claim 11 wherein said medium is distilled water.

13. The method of claim 12 wherein the concentration of said blood plasma in said distilled water is greater than zero and is up to about 25 percent by volume.

14. The method of claim 3 wherein said indicative blood serum is diluted in a medium that facilitates said step of measuring surface charges on said protein molecules.

15. The method of claim 14 wherein said indicative blood serum solution is obtained by diluting blood serum in distilled water.

16. The method of claim 15 wherein the concentration of said blood serum in distilled water is greater than zero and is up to about 25 percent.

17. The method of claim 1 wherein said laser radiation is utilized in a normal operating range of a laser which is its standard mode.

18. The method of claim 1 wherein said laser radiation is produced using a Helium Neon Laser.

19. The method of claim 1 wherein said laser radiation has a wavelength of $\lambda=632.8$ nm.

20. The method of claim 1 wherein said step of measuring is accomplished with an apparatus capable of microsecond level measurements.

21. The method of claim 1 wherein said step of measuring surface charges on said protein molecules is measured as a Rayleigh Light Scattering Factor R of said indicative solution.

22. The method of claim 21 wherein said established reference range standards are obtained from a reference solution prepared from an effective amount of blood constituents of an individual proven free of oncological disease and said step of screening for the presence of oncological disease is determined by comparing Rayleigh Light Scattering Factor R and determined parameters of effective mass M and molecular interaction R of said indicative solution with said established reference range standards when said value of R is more than two times the value of an analogous factor $R_{ref}$ from said reference solution and when the value of said effective mass parameter M of said indicative solution is greater than the value of an analogous determined effective mass parameter $M_{ref}$ of said reference solution and when the value of said parameter of molecular interaction B of scattered radiation in said indicative solution is less than the value of a determined value of $B_{ref}$ of said reference solution.

23. The method of claim 21 wherein said step of comparing includes analyzing said indicative parameters with the aid of a laboratory nephelometer.

24. The method of claim 21 wherein said laser radiation is produced with a Helium Neon Laser.

25. The method of claim 21 wherein said laser radiation has a wavelength of $\lambda=632.8$ nm.

26. The method of claim 22 wherein said step of comparing includes analyzing said indicative parameters with the aid of a laboratory nephelometer.

27. The method of claim 22 wherein said laser radiation is produced with a Helium Neon Laser.

28. The method of claim 1 wherein said laser radiation has a wavelength of $\lambda=632.8$ nm.

29. The method of claim 1 wherein said established reference range standards includes a reference solution prepared from an effective amount of blood constituents from an individual with g proven oncological disease selected from the group consisting of stomach, uterus, cervix, breast and throat.

30. The method of claim 29 wherein said step of comparing includes analyzing said indicative parameters with said analogous parameters with the aid of a laboratory nephelometer.

31. The method of claim 29 wherein said step of exposing said indicative solution to laser radiation is accomplished with a Helium Neon Laser.

32. The method of claim 29 wherein said step of exposing said indicative solution to laser radiation is accomplished by laser radiation at a wavelength of $\lambda=632.8$ nm.

33. A method for screening for the presence or absence of oncological diseases of the stomach, uterus, cervix, breast and throat comprising the steps of:

(a) obtaining an effective amount of about 0.05 ml to 0.4 ml of blood in the form of an indicative solution of blood constituents;

(b) exposing said indicative solution of blood constituents to laser radiation to cause scattered radiation from said indicative solution;

(c) measuring surface charges on protein molecules as scattered radiation values and determining parameters of effective mass M and molecular interaction B for said indicative solution at a molecular level;

(d) comparing said measured and determined parameters of said indicative solution with analogous parameters of established reference range standards;

(e) screening for the presence or absence of oncological diseases of the stomach, uterus, cervix, breast and throat based upon a comparison of said measured and determined parameters of said indicative solution with said established reference range standards.

34. The method of claim 33 further comprising the step of removing red blood cells from said blood to obtain a plasma to form said indicative solution of blood constituents.

35. The method of claim 34 further comprising the step of diluting said plasma in a medium for facilitating the measurement of parameters to form said indicative solution of blood constituents.

36. The method of claim 34 further comprising the step of removing red blood cells and clotting factors to obtain a serum to form said indicative solution of blood constituents.

37. The method of claim 36 further comprising the step of diluting said serum in a medium for facilitating the measurement of parameters to form said indicative solution of blood constituents.

* * * * *